United States Patent [19]

Rudie

[11] 4,154,241
[45] May 15, 1979

[54] ANASTOMOSIS CLAMP

[76] Inventor: Peter S. Rudie, Rm. 302, Nedical Arts Bldg., Duluth, Minn. 55802

[21] Appl. No.: 820,306

[22] Filed: Jul. 29, 1977

[51] Int. Cl.² ............................................. A61B 17/11
[52] U.S. Cl. ............................................... 128/334 C
[58] Field of Search ............... 128/334 R, 334 C, 346, 128/303 R

[56] References Cited

U.S. PATENT DOCUMENTS

| 2,434,030 | 1/1948 | Yeomans | 128/346 |
| 2,638,901 | 5/1953 | Sugarbaker | 128/334 C |
| 3,771,526 | 11/1973 | Rudie | 128/334 C |
| 4,055,186 | 10/1977 | Leveen | 128/334 C |

FOREIGN PATENT DOCUMENTS 1057729  5/1959  Fed. Rep. of Germany ....... 128/334 C Primary Examiner—Dalton L. Truluck
Attorney, Agent, or Firm—Wicks & Nemer

[57] ABSTRACT

An anastomosis clamp which includes a first clamping collar including a first sleeve having an annular flange formed on one end and overlying said first sleeve in spaced relation. A second clamping collar is provided which has a second sleeve having an annular flange formed on one end and overlying said second sleeve with the second sleeve slidable on said first sleeve with said flanges in opposed relationship for clamping bowel members therebetween. Apparatus is included for drawing the flanges together in clamping relationship and for holding the flanges in open spaced relationship. One flange has two holes in which supply tubes are positioned whereby a fluid such as an antibiotic can be introduced interiorally of the flanges. One or more of the flanges has a drain hole whereby the antibiotic can travel to points exteriorally of the clamp.

5 Claims, 7 Drawing Figures

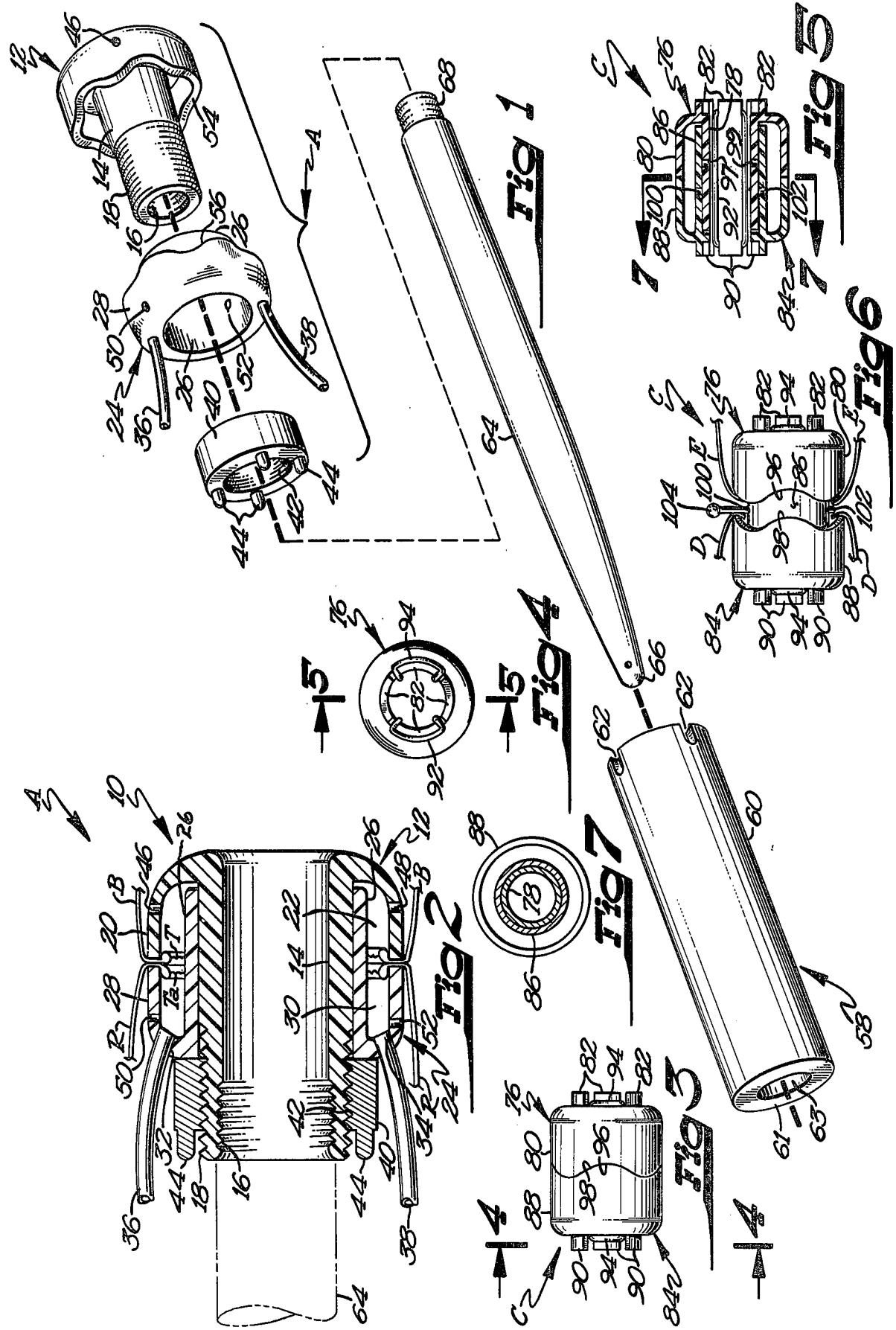

ANASTOMOSIS CLAMP

SUMMARY

The invention relates generally to clamps of the surgical type and more particularly to an improved rectocolic anastomosis clamp. After removal of a portion of the bowel, the remaining ends must be joined, and it is highly desirable to carry out bowel anastomosis by clamping together inturned ends until agglutination occurs at the periphery of the clamped junction.

With conventional clamping, the healed bowel ends usually form a joint that has a diameter less than that of the original which results in a restriction in the bowel. Also it is desirable that with the clamp in place within the bowel there may be a ready escape of mucoid contents of the bowel.

The object of the present invention is to provide a rectocolic anastomosis clamp for joining bowel ends whereby the inside diameter of the healed bowel is not restricted to less than that of the original and at the same time allow escape of the contents of the bowel through the clamp with the clamp in clamping position.

In use in the lower bowel area where the rectum is joined with the bowel one form of the clamp allows assembly of part of the clamp within the bowel with another part being extended through the rectum and anus and on which a clamp part is inserted up through the anus and rectum. With the device the clamping pressure is established and adjusted by manipulation of the clamp by the part extending outwardly of the anus. A further embodiment of the clamp is used to clamp portions of the upper or small bowel, respectively, or to clamp a portion of the small bowel to the stomach as in gastroenterostomy and in the latter embodiment there is no extension of the clamp outwardly of the anus. In the latter embodiment the parts allow free unobstructed passage of mucoid contents of the bowel through the clamp. With either embodiment the clamp is sluffed off in three or four days.

A further feature of the invention is to provide at least one hole formed in the flange of the second collar member to which a tube is connected for delivering fluid material interiorally of the flange and of a flange formed on a first collar member slidable on said first collar member. The flanges of the collars have fluid dispersing holes whereby fluid material such as antibiotics travel from within the clamp to the area surrounding the clamp.

Related prior art: U.S. Pat. No. 3,771,526.

The invention will appear more clearly from the following detailed description when taken in connection with the accompanying drawings, showing by way of example preferred embodiments of the inventive idea wherein like numerals refer to like parts throughout.

In the drawings forming part of this application:

FIG. 1 is an exploded perspective view of an anastomosis clamp including wrench and insertion rod embodying the invention.

FIG. 2 is a longitudinal sectional view of the clamp in clamping position on the ends of joined bowel members a portion of the insertion rod shown in broken lines.

FIG. 3 is a side elevational view of a further embodiment of an anastomosis clamp.

FIG. 4 is an end view thereof on the line 4—4 of FIG. 3.

FIG. 5 is a longitudinal sectional view on the line 5—5 of FIG. 4.

FIG. 6 is a side elevational view similar to that of FIG. 3 but with the half portions of the clamp locked in open position.

FIG. 7 is a sectional view on the line 7—7 of FIG. 5.

Referring to the drawings in detail, the anastomosis clamp A includes the clamping head 10. The head 10 includes the first collar 12 which has the first sleeve portion 14 threaded internally at the inner end as at 16 and threaded externally as at 18 at the same end. The outer end of the collar portion 14 terminates in the annular return flange 20 which overlies a portion of and is spaced from the sleeve 14 thereby forming an annular channel 22.

The numeral 24 designates a second collar which includes the second sleeve portion 26 the inside diameter of which is substantially that of the outside diameter of the first sleeve portion 14 so that the sleeve portion 26 can be slip fit onto the sleeve portion 14. The inner end of sleeve portion 26 terminates in the return flange 28 which overlies a portion of and is spaced from the sleeve portion 26 thereby forming an annular channel 30.

The flange 28 has formed therethrough the holes 32 and 34 in which are secured the supply tubes 36 and 38, respectively. Further provided is the screw up clamping nut 40 which is a hollow cylindrical formation threaded internally as at 42. Formed on the outer edge of the clamp nut 40 are the spaced relatively small projections 44 which extend axially of the nut 40. The flange 20 is formed with the fluid dispersing holes 46 and 48, and the flange 28 is formed with the fluid dispersing holes 50 and 52. The peripheral edge of the flange 20 is formed with undulations 54 complementary to undulations 56 of the periphery of flange 28 for clamping engagement therewith.

The numeral 58 designates a wrench for assembly of the clamp and it is formed of the hollow cylindrical portion 60 which has formed at one end thereof four spaced notches 62 that receive therein the projections 44 of the nut 40. The wrench includes the end wall 61 having the hole 63 which aligns the rod 64. The rod 64 is slightly pointed at one end as at 66 and at the other end the rod is threaded as at 68 for engagement with the threads 16 of the portion 14 of the first collar 12. The rod 64 allows guiding of the collar 24 into position on sleeve 14 and guides the nut and wrench into position.

The device A is used in the following manner to join and clamp a bowel end with the end of the rectum after a portion of the bowel has been removed.

First the rod 64 is screwed into the threads 16 of the sleeve portion 14 of the first collar 12. Then the end of bowel B is gathered about the ends of flange 20 and puckered with thread T to hold the bowel end on the flange. Meanwhile the end of the rectum R has been sewed shut by thread Ta to prevent entry of foreign matter. Then the rod 64 is forced through the sewed end of R and through the rectum portion R and extended out of the rectum. The collar 24 is then slipped onto the rod 64 up through the anus and into rectum portion R. Then the nut 40 is slipped onto the rod 64 up to the end of sleeve 14. Next the wrench 58 is slipped onto the rod 64 and engaged with the nut 40 which is drawn up against collar 24 the flange of which is moved to clamping relationship with flange 20 upon the end of rectum R and end of bowel B. The rod and wrench are then removed out the anus thereby leaving the two collars in clamping condition. After the clamped portion of bowel and rectum are healed, the collar unit is sluffed off through the anus. It will be seen that the rod allows positioning of the clamp into the rectum R and the rod guides the wrench into quick easy engagement with the projections of the nut 40 for operation thereof.

It will be further noted that the inside of the sleeve portion 14 allows unencumbered passage and ready escape of mucoid contents of the bowel through the clamp while the bowel and rectum are healing at the clamped joint. Antibiotics may be fed directly to the clamped ends of the rectum and bowel in the channels 30 and 22 by means of the tubes 36 and 38 with the tubes extending outwardly through the anus. The tubes also allow pulling of the clamp out through the anus. The holes 30, 46, 48 and 52 act as drains to disperse antibiotics exteriorly of the clamp.

In FIGS. 3-7 is illustrated a further embodiment of the invention in clamp C for joining two upper bowel ends. Clamp C includes the first clamping collar 76 which includes the sleeve portion 78 which terminates at one end in the return flange 80 which overlies portion 78. Projecting axially from the sleeve portion 78 are the spaced projections 82.

The numeral 84 designates a second clamping collar which includes the sleeve portion 86 which terminates at one end in the return flange 88 which overlies portion 86. The inside diameter of sleeve portion 86 is such that it slidably and snugly fits on sleeve portion 78 of collar 76. Projecting axially from the sleeve portion 86 are the spaced projections 90.

Rubber bands 92 and 94 are engaged upon the projections 82 and 90 thereby urging the clamping collars 76 and 84 together in clamping relation at the meshing undulated edges 96 and 98, respectively. The sleeve 78 of collar 76 is formed with opposed and aligned pin holes 97 and 99, and the sleeve 86 of collar 84 is formed with opposed and aligned holes 100 and 102. When the holes 100 and 102 are aligned with holes 96 and 98 against the action of the rubber bands 92 and 94, the pin 104 is inserted through all of the holes thereby maintaining the collars 76 and 84 in open unclamped position, particularly FIG. 6. In such a condition, the bowel end D is puckered about the end of flange 88 conventionally by means of thread, and bowel end E is puckered conventionally about the end of flange 80 by means of thread. Then the pin 104 is removed whereby the rubber bands urge the edges 96 and 98 into clamping relation upon the bowel ends D and E. When the bowel ends D and E are healed together the clamp is sluffed off in three or four days outwardly through the anus.

It will be noted that the inside of the sleeve 78 allows unencumbered passage and ready escape of mucoid contents of the bowel through the clamp C when it is operative clamping condition.

Having thus described the invention, what is claimed as new and desired to be secured by Letters Patent is:

1. An anastomosis clamp comprising:
   (a) a first clamping collar including a first sleeve having
   (b) an annular flange formed on one end and overlying said first sleeve in spaced relation,
   (c) a second clamping collar including a second sleeve having
   (d) an annular flange formed on one end and overlying said second sleeve,
   (e) said second sleeve slidable on said first sleeve with said flanges in opposed relationship,
   (f) means for drawing said flanges together in clamping relationship,
   (g) means for actuating said means for drawing said flanges together
   (h) means for guiding said actuating means, said means for drawing said flanges together including
   (i) threads formed on said first sleeve,
   (j) a nut threadedly engaged with said threads of said first sleeve, said means for actuating said drawing means including a tubular wrench adapted to slip over said guiding means into engagement with said nut.

2. The device of claim 1, in which said means for guiding said actuating means includes
   (a) a rod with
   (b) means for engaging one end of said rod with said first mentioned sleeve.

3. An anastomosis clamp comprising:
   (a) a first clamping collar including a first sleeve having
   (b) an annular flange formed on one end and overlying said first sleeve in spaced relation,
   (c) a second clamping collar including a second sleeve having
   (d) an annular flange formed on one end and overlying said second sleeve,
   (e) said second sleeve slidable on said first sleeve with said flanges in opposed relationship,
   (f) means for drawing said flanges together in clamping relationship,
   (g) means for actuating said means for drawing said flanges together,
   (h) means for guiding said actuating means, and
   (i) means for introducing a fluid interiorally of said flanges to treat anatomy members clamped between said flanges.

4. The device of claim 3 in which said introducing means includes
   (a) a hole in at least one of said flanges in which
   (b) a tube is inserted for extension out of the anus.

5. The device of claim 4 in which at least one of said flanges is formed with a fluid dispersing hole.

* * * * *